United States Patent [19]
Palenscar

[11] 3,951,609
[45] Apr. 20, 1976

[54] SAMPLING APPARATUS
[76] Inventor: William J. Palenscar, 3788 Highland Drive, Carlsbad, Calif. 92008
[22] Filed: Sept. 3, 1974
[21] Appl. No.: 502,774

[52] U.S. Cl. ............................... 23/259; 23/253 R; 356/72; 356/244
[51] Int. Cl.² ................... G01N 21/24; G01N 33/16
[58] Field of Search ............ 23/259, 253 R; 356/72, 356/244

[56] References Cited
UNITED STATES PATENTS

| | | | |
|---|---|---|---|
| 3,192,968 | 7/1965 | Baruch et al. | 23/259 X |
| 3,763,705 | 10/1973 | Strande | 23/259 X |
| 3,788,816 | 1/1974 | Rohrbaugh et al. | 23/259 X |

*Primary Examiner*—Robert M. Reese
*Attorney, Agent, or Firm*—Georges A. Maxwell

[57] ABSTRACT

A sampling apparatus for sequentially testing a plurality of samples by sequentially lowering the samples in a sample testing means and which includes a standard photographic slide projector and slide tray wherein the projector has a vertically upwardly opening gate, said tray has a plurality of vertically upwardly and downwardly opening slide slots and said projector has power driven means for moving the tray to sequentially advancing the slots into and out of register with the gate and power driven transport means to elevate slides dropped from each slot into the gate back up into the slot; a plurality of slide-like test sample carriers engaged in the slots to project upwardly therefrom and shiftable into and out of engagement in the gate, arms projecting from the bodies and having terminal ends spaced from the projector and about the testing means and test sample handling means at said ends of the arms to support samples to be lowered into the testing means when the body of each carrier is shifted vertically in and between the gate and its related slot.

12 Claims, 8 Drawing Figures

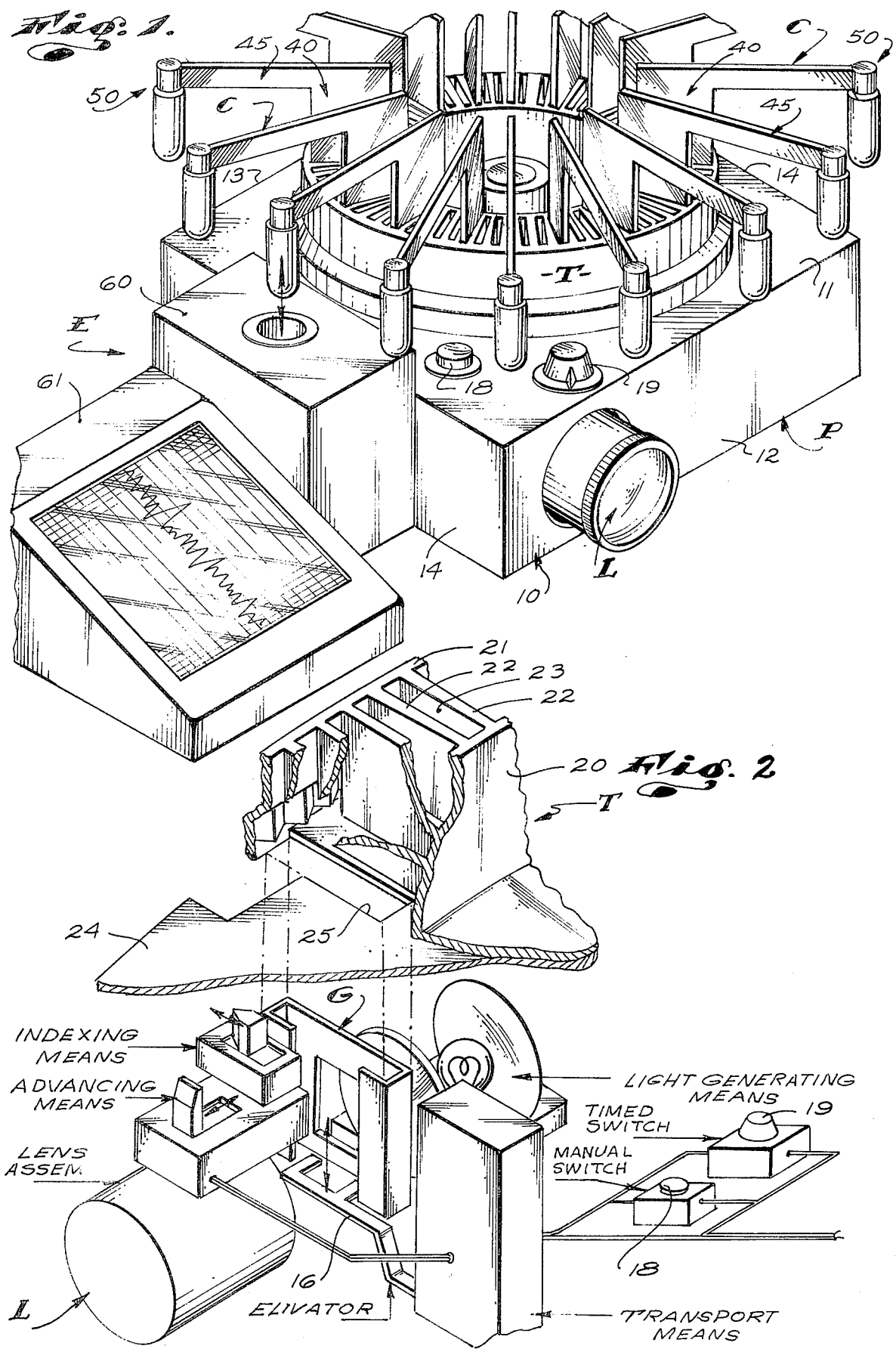

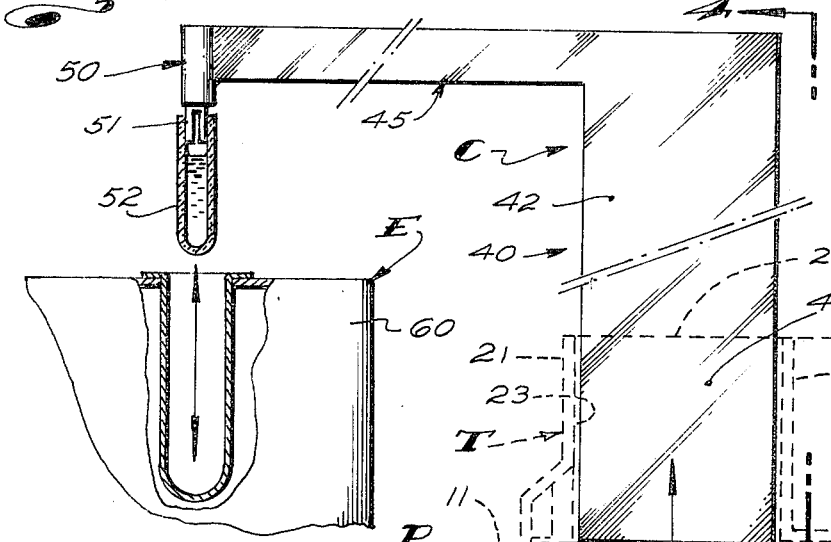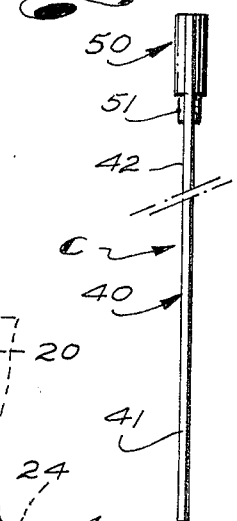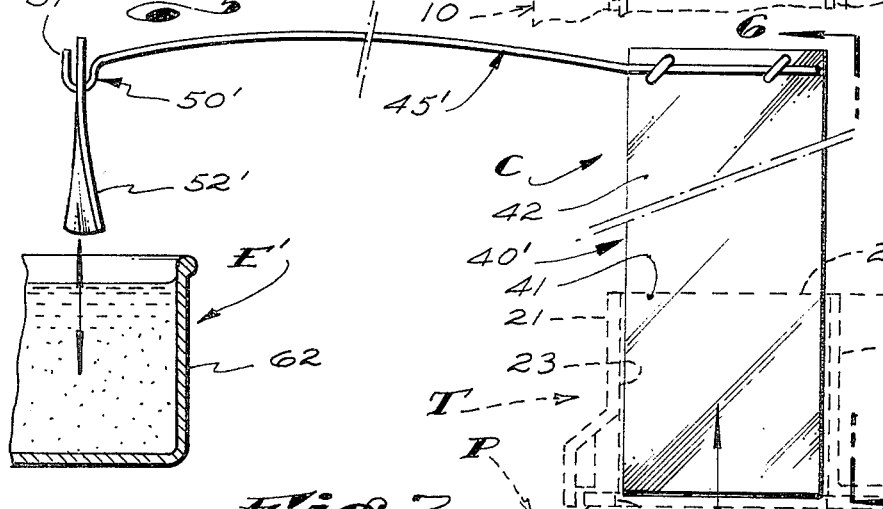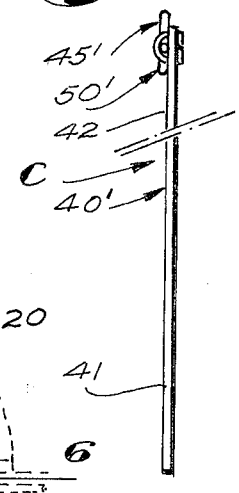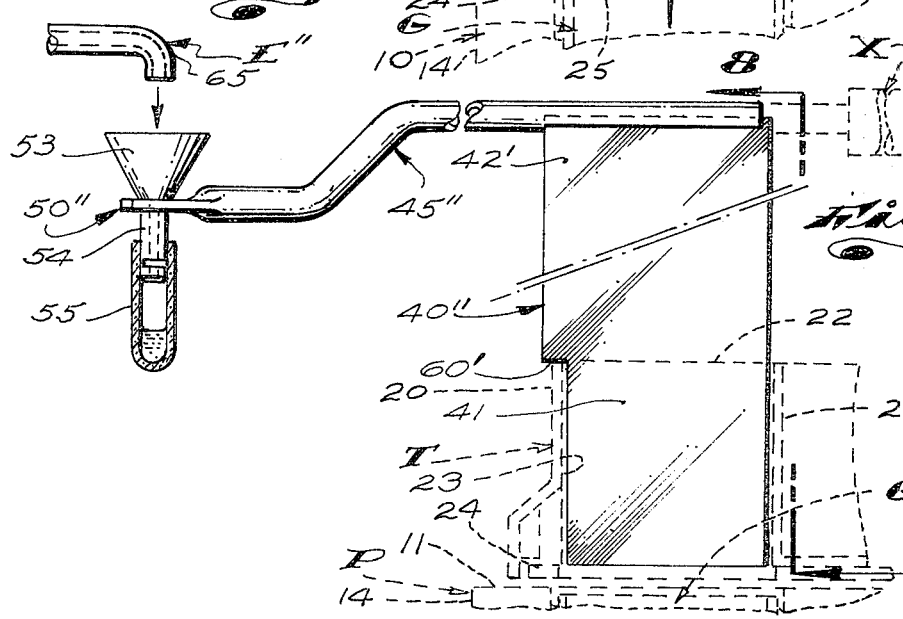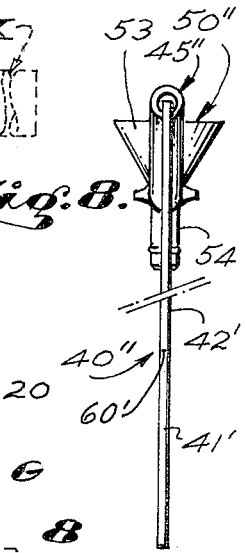

SAMPLING APPARATUS

This invention has to do with an automatic sampling means and is more particularly concerned with means for carrying and sequentially advancing a multiplicity of samples to and from an inspection station and transporting each of said samples at said stations into and out of cooperative relationship with appropriate sample testing or analyzing means at said station.

Throughout the art there are many instances where small samples of matter must be collected and/or suitably examined or tested. In a considerable number of such instances, a multiplicity of such samples are collected in some particular order with respect to time or some other appropriate standard or reference factor and must be examined and/or tested in corresponding order.

Typical instances where a multiplicity of samples are collected in timed, sequential order and must be examined or tested in corresponding order are, radioassays or radioimmunoassays of human blood, wherein a radioactive material is introduced into a patient's blood stream at one location; a multiplicity of blood samples are obtained from the patient at another remote location at timed intervals and the samples are thereafter tested for traces of radioactivity in the same order in which they were taken. It will be apparent that such testing of blood is valuable in determining the condition of a patient's cardio-vascular system and can be of special value in diagnosing and testing various special or particular human ailments.

In carrying out the above noted assays, the samples of blood, taken one at a time, are placed in small vials or test tubes and the tubes are arranged in a suitable rack, in order. Subsequently, upon testing the samples, the test tubes are manually engaged, one at a time, in a scintillator with a related recording device and are thereafter manually replaced in the rack. The manual handling and manipulation of the test tubes is time consuming, tiresome, and, as a result, is quite subject to human error.

It is understood that in efforts to eliminate the burdens and potential errors associated with the sequential manual handling of multiplicities of samples, such as noted above, the prior art has provided special mechanical means and equipment into which the same can be arranged and which thereafter automatically affects the testing of the samples. Such means, to the best of my knowledge, have been large, complicated and extremely costly, custom-built or one of a kind type means or apparatus and are of questionable effectiveness and dependability.

Typical of another instance where a multiplicity of samples are taken or obtained in a fixed order and are thereafter tested in like order is where the turbidity of a fluid is sought to be monitored. In such case, a fraction collector is employed to obtain samples of the fluid, drop by drop in separate test tubes and the samples are thereafter os simultaneously tested by means of a suitable turbidimeter.

In another known instance, the pH factor of a fluid must be regularly monitored. To this date monitoring of that fluid is effected manually by dipping pieces of litmus paper into the fluid at timed invervals. Such a practice requires the constant attention of a specially trained person and is not only costly but is subject to human error.

It is to be understood and it will be readily appreciated that the several examples of testing procedures briefly described above are not exclusive of sequential and orderly sampling and testing of materials but rather, are only illustrative of the extensive and diversified practice of such sampling and testing of materials.

An object of my invention is to provide a simple, inexpensive, highly effective and dependable means for carrying and sequentially advancing a multiplicity of test samples into adjacent proximity with a related inspection or testing station, transporting the samples into and out of said station and thereafter advancing the samples from said station.

It is an object and feature of this invention to provide a means of the character referred to which includes and utilizes a standard, relatively inexpensive machine which is mass-produced and is distributed and serviced throughout the world, in combination with a plurality of like, small, light, simple, easy and economical to make, package and transport, adapter-like carrier parts whereby the means here provided can be advantageously and economically established or made up and can be serviced throughout the world.

An object and feature of the present invention is to provide a means of the character referred to which includes a standard photographic slide projector with slide tray indexing or advancing means and slide transporting means, a compatible slide tray related to the projector and a multiplicity of slide-like test sample carriers shiftably engaged in and with the tray and a means wherein the indexing means of the projector indexes the tray to sequentially advance the test sample carriers carried thereby relative to a testing station related to the projector and said slide transporting means of the projector operates to shift each of said carriers advanced to said station relative to the tray whereby test samples carried by carriers are transported into and out of a predetermined testing disposition at or in said station.

Yet another object and feature of the instant invention is to provide simple inexpensive and practical slide-like test sample carriers cooperatively related with a standard photographic slide projector and slide tray whereby slide advancing means and slide transporting means of the projector function to sequentially advance and transport the carriers to position test samples, carried thereby into and out of predetermined testing disposition.

Still another object and feature of my invention is to provide test sample carriers, the design of which can be conveniently altered or varied as circumstances require or as desired.

The foregoing and other objects and features of my invention will be apparent and will be understood from the following description of typical preferred forms and applications of the invention throughout which description reference is made to the accompanying drawings, in which:

FIG. 1 is an isometric view illustrating the apparatus provided by the present invention;

FIG. 2 is an isometric diagrammatic view of certain portions and means of the projector structure provided;

FIG. 3 is a side view of a sample carrier that I provide;

FIG. 4 is a view taken substantially as indicated by line 4—4 on FIG. 3;

FIG. 5 is a side view of another form of sample carrier;

FIG. 6 is a view taken as indicated by line 6—6 on FIG. 5;

FIG. 7 is a side view of yet another form of sample carrier; and

FIG. 8 is a view taken as indicated by line 8—8 on FIG. 7.

Referring to the drawings, the structure that I provide includes generally, a power driven automatic slide projector P, a compatible slide tray T, test sample carriers C and related testing equipment E.

The projector P is preferably that basic slide projector structure or machine manufactured by Kodak Company and sold under the tradename "Carousel". More specifically, the projector P is preferably one of the several modes of Carousel projectors in the H series of said projectors, such as Model No. 800-H.

The projector P, that is the "Carousel" projector here employed and which is illustrated in a substantially diagrammatic manner in the drawings, basically includes or comprises a box-like housing 10 which is substantially square in plane configuration and characterized by a substantially flat top wall 11 and front, rear and side walls 12, 13 and 14. Within the housing 10 there is provided a projecting means comprising a lens assembly L, a light generating means (not shown) and a gate G between the lens assembly and light generating means to accommodate photographic slide (transparencies within apertured, flat, square paper frames or carriers). The lens assembly and light generating meanas are in axial alignment and extend from the front to the rear of the housing with the front end of the lens assembly opening or exposed at the front wall 12. Further, the said lens assembly and light generating means occur within the housing adjacent one side wall 14 thereof, for example, the right hand side wall (with respect to the front and rear of the housing). The gate G opens upwardly at the top wall 11, adjacent the right hand side thereof and substantially midway between the front and rear of the housing. The gate G is shown as a simple opening in the top wall of the housing. In practice, the gate is designed and constructed to freely accommodate slides dropped therein from within the tray T at the top of the housing and to properly orient and hold the slides relative to the lens assembly for projection purposes.

In addition to the above, the housing is provided with a spindle which projects freely upwardly from the central portion of the top wall 11 of the housing to rotatably orient the tray T and accommodates power driven tray advancing and/or indexing means which is operable to intermittently drive or rotate the tray T a predetermined fraction of a revolution.

The housing 10 next accommodates power driven transport means related to the gate G and the tray T and which means is suitably timed with the indexing means and operates to transport slides in the gate, vertically, back into the tray T. The transport means characteristically includes a vertically shiftable elevator 16 which normally occurs adjacent the bottom of the gate and functions to urge and move slides, dropped into the gate from the tray T, up and back into engagement with the tray.

In addition to the foregoing the projector can be provided with other operating support means and devices such as an on and off control switch, switches for the light generating means and blower, a manually operable pressure switch 18 for the indexing means and an automatic timing device for said indexing means.

The switches and timing device are such that the projector can be operated without the light generating means on and such that the indexing means and transport means can be operated or cycled by means of the referred to manually operated switch 18 or can be set to operate automatically by setting the noted timing device by means of a control knob 19.

Since the exact nature and make up of the several above noted means of the projector P and of the electrical circuitry employed does not go to and affect the novelty of this invention and can be varied substantially, I have elected not to burden this disclosure with detailed illustration and description thereof and have elected to illustrate those details of the projector construction which are deemed necessary and have shown them in a general or diagrammatic manner.

The slide tray T is that type and construction of slide tray provided for use in connection with Kodak Carousel projectors and are produced, distributed and sold by Kodak Company.

The slide tray T is an annular unit characterized generally by annular, molded plastic body with vertical, inside and out side walls 20 and 21 and a plurality of vertical, radially extending, circumferentially spaced partitions 22 between the walls 20 and 21 and defining a plurality of circumferentially spaced, radially extending and vertically upwardly and downwardly opening slide receiving slots 23. The diametric extent of the tray is such that the slots 23 overlay the gate G of the projector P as the tray is rotated relative thereto. In addition to the above, the tray is provided with a bottom wall 24 rotatably carried by or rotatably carrying the body and overlying the bottoms of the slots 23. The bottom wall 24 is characterized by a central spindle receiving opening in which the spindle on the top wall of the projector enters, orienting means to hold bottom wall in fixed rotative position and a slide conducting aperture 25 in vertical alignment with the projector gate G. The bottom wall 24 is further provided with releasable slide retaining means adjacent the opening 25 to releasably retain the slides in the slots 23 when in register with the aperture 25 and which is adapted to be momentarily released by suitable trigger means at the top of the projector and to thereby release and permit the slide in each slot to drop therefrom, downwardly, into the gate G as each slot is indexed or advanced into register with the gate. The referred to retaining means is such that when a slide is elevated back, up and into its related tray slot, the slide is retained therein as the tray body is advanced from in register with the gate.

It is to be noted and understood that the drawing here provided and the foregoing description of the tray T is diagrammatic and brief in nature and is merely intended to set forth the basic nature and class of tray employed and the basic cooperative relationship of the tray with the projector.

Accordingly, all of the referred to means provided in the tray construction and the related means of the projector P are not shown or illustrated and only portions of those means which might serve to best define or qualify the projector P as a Kodak Carousel projector are diagrammatically illustrated or shown in phantom lines.

With the structure here provided, as the projector P is operated to rotate the tray T and sequentially index and advance the slots 23 thereof into vertical alignment with the gate G (under control of the manual switch 18 or automatic timer), the noted latch means releases the noted retaining means as each tray slot moves into register with the projector gate and the slide or any slide-like part arranged in that slot drops downwardly into the gate. When the projector is operated or actuated to again index or advance the tray, the transport means or elevator first moves the slide or slide-like part in the gate, vertically upwardly and back into its related slot 23 and the tray is then indexed or moved to advance the next, adjacent slot into register with the gate and to thereby complete each indexing cycle of the construction.

In carrying out the instant invention, the projector P and tray T described above are utilized but the light generating means and the projecting lens assembly L of the projector are left out of service or are not utilized. Accordingly, for the purpose of carrying out this invention, a Kodak Carousel without the expensive lens assembly and lamp or light generating means normally included therein can be purchased at a substantial reduction in cost.

It is to be noted that the tops or upper ends of the slots 23 of the tray T are open for convenience and to normally facilitate manual removal and engagement of slides in the tray, when it is in use.

In practice, trays T adapted to hold different numbers of slides are provided. For example, trays for 140 slides and trays for 80 slides are commonly marketed.

The instant invention next includes the aforementioned text sample carriers C. The carriers C are novel, flat, plate-like parts which can be advantageously established from 1/16 inch thick plastic sheet stock or the like and have elongate, flat, vertical, rectangular bodies 40 with lower portions 41 corresponding dimensionally with standard slides, that is, which are 2¼ inch × 2¼ inch, and upper portions 42 formed integrally with and continuing upwardly from said lower portions. The lower portions 41 of the carriers are adapted to be releasably engaged in related slots 23 of the tray T and to be selectively dropped or lowered into the gate G of the projector and subsequently elevated from the gate and re-engaged in the tray slot in the same manner as standard slides.

The upper or top portion 42 of the carriers normally project freely upwardly from their related tray slots 23 and lower or move downwardly into engagement in said slots, in whole or in part, when their related lower portions 41 are dropped or lowered into the projector gate, as noted above. The upper portions 42 move upwardly to their normal position upon return of their related lower portions, from within the gate G into their related slots 23.

In the preferred carrying out of the invention, the upper portions 42 of the carriers normally project above the tray T a distance equal to or greater than the vertical stroke of the projector P, that is 2¾ inch or more.

The carriers next include and are characterized by laterally outwardly projecting support or carrier means 45, which means are arranged to project radially outwardly from the tray, with respect to the axis thereof and which are of sufficient radial extent so that their outer ends or outer end portions occur laterally outward of or from the outer peripherey of the projector housing 10, about the entire perimeter thereof or, at least, laterally outward of the right hand side of the housing 10, adjacent the gate G, when the carriers are aligned with the gate.

In practice, the support means 45 are in the nature and form of simple, elongate, substantially horizontal arms fixed to or joined integrally with the upper ends of the bodies 40 and are provided with sample handling means 50 at their outer ends.

In practice, the support means or arms 45 can be varied in length and can be inclined upwardly or downwardly and/or can be curved or angularly formed to meet special requirements, without departing from the spirit of my invention. In the drawings, I have shown several forms of carriers, each of which has a distinct form of support means.

The sample handling means 50 that I provide can be varied widely in form. For example, and as shown in FIGS. 3 and 4 of the drawings, the means 50 are in the form of vertical plug-like parts 51 at the ends of the arms 45 and on and about which small, glass, sample carrying test tubes 52 are snugly engaged. In FIGS. 5 and 6 of the drawings, the arm 45' is an elongate spring wire part or element fixed to the body 40' as by staples is a simple hook 51' at the end of the wire on which a test sample or a piece of testing material, such as litmus paper strip 52' can be conveniently engaged. In FIGS. 7 and 8 of the drawings, the arm 45'' is established of tube stock and the sample handling means 50'' comprises an upwardly opening funnel 53 with a depending tubular neck 54 on and with which a test tube 55 is engaged. This latter form of sample handling means is provided for use when the invention is to be employed as a fluid fraction collector.

In the latter form of carrier, where vertical movement of the sample handling means 50'' may not be necessary and may in fact be undesirable, the upper portion 42' of the carrier body 40'' may, as shown, be made wider or greater than 2½ inch in radial extent so as to establish a stop shoulder 60' which normally engages the upper edge of the adjacent inside or outside wall of the tray T and stops or prevents the carrier from dropping into engagement in the projector gate. In such a case, only the indexing and advancing means of the projector P is utilized.

The several forms of carrier C illustrated and described above are not exclusive of the forms in which the carriers can be established, but rather are merely illustrative of typical diverse forms in which such carriers can be provided.

In operation and use, the structure thus far described is cooperatively related to desired testing equipment and means E. The testing equipment is normally arranged in close proximity to the right hand side of the projector P in radial alignment with the axis of the tray T and projector gate G. Additionally, the testing equipment is arranged to normally occur clear of and below the test samples or the sample handling means 50 a limited distance so that said test sample or means 50 can be freely transported across or above the testing equipment, but a distance no greater than the above noted vertical stroke of the projector, that is, about 2¾ inch, so that upon vertical lowering of the carriers, in and by the projector P, the test samples are lowered into cooperative relationship with the testing equipment. The equipment E can as illustrated, include a radiation detector or scintillator unit 60 with a related recording means 61 adapted to cooperatively receive the test tubes 52 when each is lowered by operation of the projector P.

The unit 60, in combination with the remainder of the structure here provided is particularly suitable in conducting radioassays.

Alternatively, as when the turbidity of fluid test samples in the tubes is sought to be monitored, the scintillator unit 60 is replaced by a turbidimeter.

As diagrammatically illustrated in FIG. 5 of the drawings, the test equipment E' can be a simple upwardly opening basin 62 through which fluid to be monitored is circulated and into which the litmus paper strips 52' are sequentially dipped.

In FIG. 7 where the sample handling means 50'' of the carriers include funnels 53 and the structure is employed as a fluid fraction collector, the part or portion of the testing equipment E'' directly related to the carriers and which, for example, includes the discharge end of a fluid tap line 65 or the like, is arranged at one predetermined point above the circular path of the carriers, substantially as shown.

It will be apparent from the foregoing that the present invention, by virtue of the novel carriers C here provided, and by virtue of their special and novel relationship with the projector P and tray T, a novel, highly effective, dependable and both easy and economical to make and service automatic sampling means, for sequentially testing a multiplicity of samples, is provided.

In practice, if the arms of the carrier means are excessively long and/or heavy, or if the sample and/or sampling handling means is excessively heavy, so as to cause the carrier body to bind in the tray T, the binding effect of the excessive weight can be easily and effectively compensated for by providing the carrier with a counter balance weight, such as is shown in dotted lines at X, in FIG. 7 of the drawings.

Having described typical preferred forms and applications of my invention, I do not wish to be limited to the specific details herein set forth but wish to reserve to myself any modifications or variations which may appear to those skilled in the art and which fall within the scope of the following claims.

Having described my invention, I claim:

1. In combination, a photographic slide projector comprising an upwardly opening gate, light generating means and a lens assembly related to the gate, orienting means to support a horizontally disposed slide tray with a plurality of vertical upwardly and downwardly opening slide receiving slots in lineal series, power driven advancing means to intermittently shift the tray to sequentially move said slots into and out of vertical alignment with the gate and power driven transport means including an elevator related to the gate and shiftable vertically to transport a slide dropped into the gate from a slot when that slot is moved into alignment therewith, upwardly into returned engagement in said slot preparatory to moving said slot out of alignment with the gate; a plurality of sample carriers with flat, vertical slidelike bodies with portions slidably engaged and normally positioned within the slots in the tray and having portions projecting upwardly therefrom, carrier means at the upper portions of the bodies and projecting laterally therefrom and clear of the projector, sample handling means on said carrier means remote from the projector; said sample handling means shiftable sequentially into and out of vertical alignment with sample handling equipment spaced laterally from the projector.

2. The combination set forth in claim 1 wherein the body of each carrier is a flat, vertical part with top, bottom and side edges and has a lower portion normally engaged in a tray slot and selectively shiftable vertically into and out of engagement in said gate and has an upper portion normally projecting upwardly from and selectively shiftable vertically into and out of engagement in its related slot, whereby the carrier means and test sample handling means carried thereby are shifted vertically when said lower portions of the body are shifted into and out of engagement in said slot.

3. The combination set forth in claim 2 wherein the support means comprises an elongate arm with an inner end secured to the upper portion of the body and a free end spaced laterally from said body, said test sample handling means is at the free end of the arm and supports a test sample arranged below the outer end of the arm whereby a test sample related thereto is shifted vertically downwardly and then upwardly with respect to the normal vertical position of the carrier when the body thereof is shifted vertically relative to the gate and the slot.

4. The combination set forth in claim 3 which further includes sample testing means below the sample handling means of each carrier when said carrier is in vertical alignment with the gate and positioned vertically to occur below the test sample when said carrier is in its normal position and to receive said test sample when the carrier and the sample are shifted vertically downwardly.

5. The combination set forth in claim 1 wherein the body of each carrier is a flat, vertical, substantially rectangular part, with top, bottom and side edges, said support means comprises an elongate substantially horizontal arm projecting adjacent the top edge thereof and projecting laterally freely therefrom and wherein said sample handling means is at the free end of the arm.

6. The combination set forth in claim 5 wherein the arm is formed integrally with the body.

7. The combination as set forth in claim 5 wherein the arm is an elongate part with inner and outer ends and its inner end is secured to the body.

8. The combination set forth in claim 1 wherein said sample handling means of each carrier comprises a releasable test sample engaging device carried by an arm.

9. The combination set forth in claim 8 wherein said releasable, test sample engaging device comprises a test sample receptacle and means on the arm holding said receptacle.

10. The combination set forth in claim 8 wherein said releasable test sample engaging device comprises a test sample receptacle below the arm to depend freely therefrom.

11. The combination set forth in claim 8 wherein said test sampling handling means includes an upwardly opening fluid receiving funnel and means securing the funnel to the arm.

12. The combination set forth in claim 8 wherein said test sample handling means includes an upwardly opening fluid receiving funnel, a test sample receptacle communicating with the funnel and means securing the funnel and receptacle and funnel to the arm.

* * * * *